United States Patent [19]

Andersson

[11] Patent Number: 4,505,678
[45] Date of Patent: Mar. 19, 1985

[54] TARTAR REMOVAL INSTRUMENT

[76] Inventor: Bror A. E. Andersson, Österängsvägen 24, S-182 76 Enebyberg, Sweden

[21] Appl. No.: 554,117

[22] Filed: Nov. 21, 1983

[30] Foreign Application Priority Data

Nov. 19, 1982 [SE] Sweden .............................. 8206610

[51] Int. Cl.³ .............................................. A61C 17/00
[52] U.S. Cl. .................................................. 433/143
[58] Field of Search ....................... 433/141, 142, 143

[56] References Cited

U.S. PATENT DOCUMENTS 1,663,826  3/1928  Bier .................................... 433/141

FOREIGN PATENT DOCUMENTS 511967  4/1929  Fed. Rep. of Germany ...... 433/141

Primary Examiner—Robert Peshock
Attorney, Agent, or Firm—Young & Thompson

[57] ABSTRACT

An instrument for removing tartar consists of a handle having a working portion with its outer end formed into a blade dimensioned to be moved down along the tooth and below the gum recess. The side and end edges of the blade are rounded-off to obviate damage to the gum. For scraping or planing off tartar or other deposits on the tooth, the end portion of the blade has a through-opening with edges made as cutting edges with a relatively large cutting angle.

4 Claims, 6 Drawing Figures

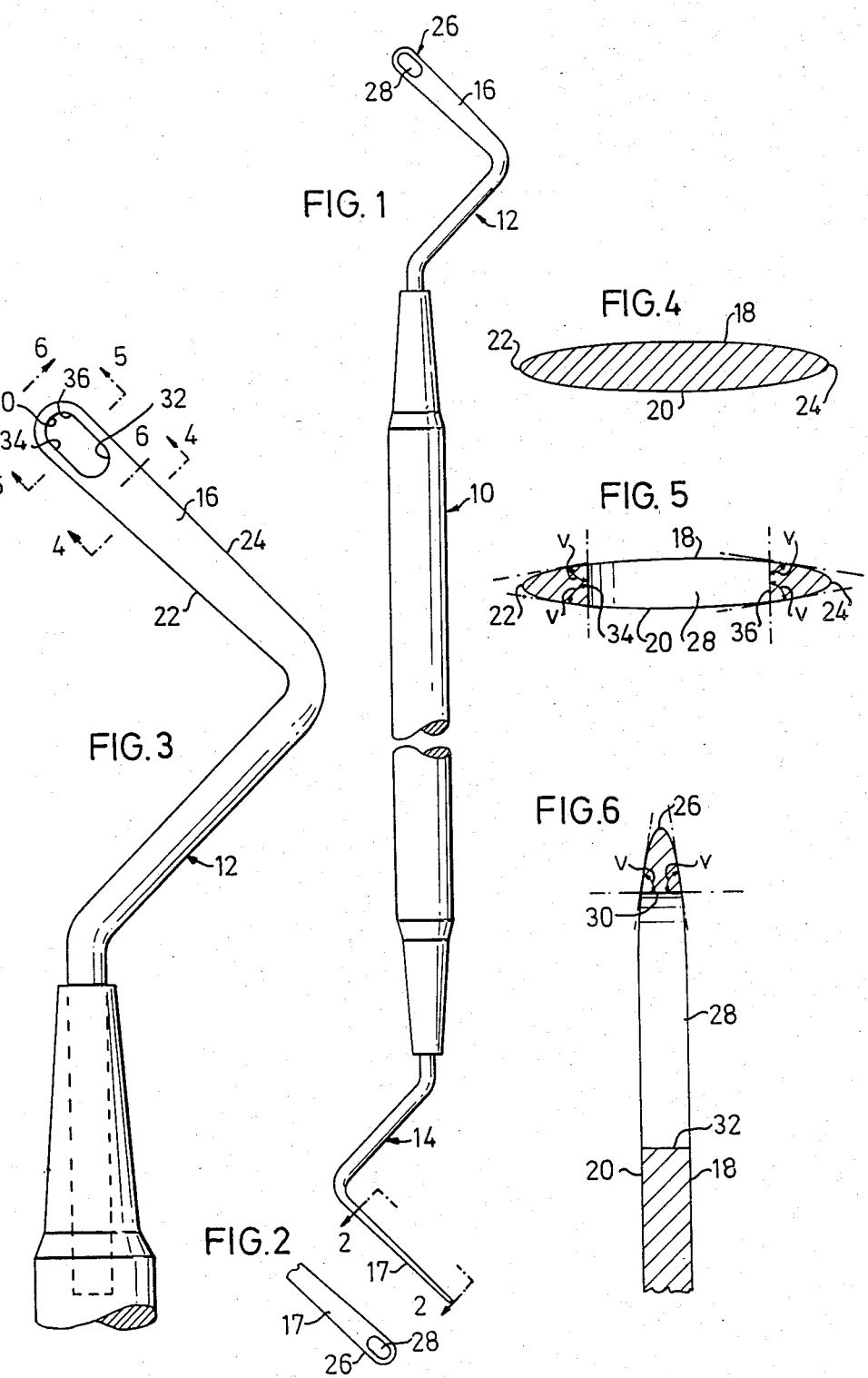

TARTAR REMOVAL INSTRUMENT

The present invention relates to an instrument for removing tartar from teeth by means of scraping. A number of different instruments for this purpose are known. The invention relates to the type of instrument consisting of a handle which, at least at one end, is provided with a steel working part formed with a sharp edge or tip for scraping a tooth clean.

The operator is usually a dentist or a dental hygienist, who must work with great concentration and care with the known instruments so that the sharp edge of the working portion does not cut into the gum and cause injuries. Examples of known instruments for the removal of tartar by scraping will be seen from the U.S. Pat. Nos. 1,138,355 and 2,552,134.

The object of the present invention is therefore to provide an instrument enabling scraping away tartar and other coatings on teeth above the gum line as well as below it, with substantially less risk of damaging the gum or the tooth enamel than is the case with the known instruments.

In a preferred embodiment of the invention, the working portion includes a thin and narrow steel blade with rounded side edges and rounded end edge, the dimensions of the blade being such that it can be inserted into the space between a pair of juxtaposed teeth, or down along a tooth and below the surrounding gum. In accordance with the invention, a through-opening with sharp edges is made in the end portion of the blade. When the opening is moved over the area where there is tartar, the rounded side edges and end edge of the blade will protect the gum from the sharp scraping edges of the opening in all movements of direction.

All in accordance with the position of tartar on the tooth, the blade with the opening may be given movements backwards and forwards lengthwise or sideways or a combination of these movements, simultaneously as the blade is pressed against the tooth and the angle of the blade in relation to the tooth surface is adjusted for obtaining the desired scraping. The cutting angle of the scraping edges is suitably in the range of 60° to 90°, preferably about 80°. During the scraping process, the instrument in accordance with the invention will essentially function as a plane which scrapes away the tartar or planes thin layers until the tartar is removed.

The instrument in accordance with the invention requires substantially less concentration and carefulness in the operator than known instruments. Consequently, it is less of a strain to work with the inventive instrument, while at the same time quicker movements can be used without risking damage to the gums if the instrument should slip.

A suitable embodiment of the instrument in accordance with the invention is illustrated as an example on the accompanying drawing.

FIG. 1 is a side view of an instrument in accordance with the invention, with a working portion on either end, FIG. 2 is a detail depiction of one working portion seen in a view according to the line 2—2 in FIG. 1, FIG. 3 is an enlarged detail depiction of the other working portion, FIG. 4 is a cross section along the line 4—4 in FIG. 3, to a further enlarged scale, FIG. 5 is a cross section along the line 5—5 in FIG. 3, and FIG. 6 is a partial section along the line 6—6 in FIG. 3.

At either end, the handle 10 is provided with a working portion 12 and 14, respectively. Both these portions consist of an arm bent into an angle and having its outer portion flattened to a thin and narrow blade 16 and 17, respectively. Only the blade 16 is described hereinafter, since the blade 17 is identical to it, but with the difference that blade 17 is turned 90° in relation to blade 16.

At the end portion of the blade 16, the thickness is suitably about 0.5 mm and the width suitably about 3 mm. The cross section of the blade according to FIG. 4 is substantially elliptical, either side 18 and 20 of the blade forming convex surfaces.

The side edges 22,24 of the blade are rounded-off, as well as its end edge 26, which furthermore has a rounded configuration merging into the straight side edges.

With this implementation, the blade may easily be moved down along a tooth and below the gum line without damaging the gum. The end portion 26 of the blade can be moved backwards and forwards in all directions below the gum line without damaging the gum.

In accordance with the invention, a through-opening 28 is made in the end portion 26 of the blade, and this opening can have any configuration, but in the illustrated embodiment it consists of two semi-cylindrical end portions 30,32 united by straight side walls 34,36, so that the opening is given a longer extension in the longitudinal direction of the blade than in its transverse direction.

As will be seen from FIG. 5, the side edges of the opening will form cutting edges with an angle v which is suitably less than 90°, preferably about 80°. At the rear end portion 32 of the opening, the angle v is equal to 90°, however, for simplifying manufacture, but if so desired the angle v between the wall of the opening and the closely adjacent surface of the respective side of the blade may be formed here as well with a cutting angle of about 80°. In practice it has been found sufficient to obtain scraping or planing during the pulling movement in reciprocating movements either longitudinally or transversely.

As will be seen from FIG. 5, the blade must be applied at a certain angle in relation to the surface which is to be scraped or planed. The blade is then pressed against the surface simultaneously as it is moved backwards and forwards. Since the cutting angle is relatively large and within the range of 60°-90°, preferably about 80°, there is very little risk that the edge will bite into the enamel, in contradistinction to known edged tools with a relatively small edge angle, which involve the risk that the edge can cut down into the enamel and damage it.

The large cutting edge also has the advantage that the edge does not cut into the gum, but glides along the underside of the gum without damaging it.

If the blade should slip when the operator is using it, one of its rounded-off side edges or the end edge will come against the gum, which is thus not damaged by any cutting edge.

What I claim is:

1. An instrument for removing tartar, including a handle having at least at one end a steel working portion formed with a sharp edge for scraping a tooth clean, characterized in that the working portion consists of an arm the free end portion of which has dimensions such that it can be moved into the space between a pair of juxtaposed teeth or along a tooth and down below the gum line; in that the end portion has rounded-off edges to obviate damage to the gum; and in that said end portion is made with at least one through-opening which at least at one end of the opening has an edge which at least along a part of the periphery thereof is formed into a scraping edge with a predetermined cutting angle, the end portion of the arm forming a blade both sides of which are convex so that the cutting angle at the edges of the opening will be less than 90°, at least along the greater portion of the periphery of the respective edge.

2. An instrument as claimed in claim 1, in which the extent of the opening in the longitudinal direction of the end portion is greater than the width of said opening.

3. An instrument as claimed in claim 1, in which said cutting angle is at least as great as 60°.

4. An instrument as claimed in claim 1, in which said free end portion of said arm surrounding said opening has a width substantially greater than its thickness.

* * * * *